United States Patent
Urushiya

(10) Patent No.: US 7,061,533 B1
(45) Date of Patent: Jun. 13, 2006

(54) IMAGE PROCESSING APPARATUS

(75) Inventor: Hiroyuki Urushiya, Omiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/544,167

(22) Filed: Apr. 6, 2000

(30) Foreign Application Priority Data

Apr. 8, 1999 (JP) ................................. 11-101205

(51) Int. Cl.
*H04N 5/232* (2006.01)
*G06K 9/40* (2006.01)
*G01N 23/201* (2006.01)

(52) U.S. Cl. .......................... 348/346; 382/254; 378/87

(58) Field of Classification Search ................ 348/246, 348/247, 420.1
See application file for complete search history.

(56) References Cited

U.S. PATENT DOCUMENTS

| | | | | |
|---|---|---|---|---|
| 4,703,442 A | * | 10/1987 | Levine ........................ | 384/244 |
| 4,805,023 A | * | 2/1989 | Younse et al. ............... | 348/247 |
| 5,185,883 A | * | 2/1993 | Ianni et al. .................. | 348/247 |
| 5,400,076 A | * | 3/1995 | Iwamura ................ | 375/240.15 |
| 5,621,467 A | * | 4/1997 | Chien et al. ........... | 375/240.15 |
| 5,805,216 A | * | 9/1998 | Tabei et al. .................. | 348/246 |
| 5,917,935 A | * | 6/1999 | Hawthorne et al. ......... | 382/149 |
| 5,982,946 A | * | 11/1999 | Murakami ................... | 382/275 |
| 6,002,433 A | * | 12/1999 | Watanabe et al. ........... | 348/246 |
| 6,301,392 B1 | * | 10/2001 | Acharya ..................... | 382/239 |
| 6,573,927 B1 | * | 6/2003 | Parulski et al. .......... | 348/231.7 |
| 6,611,288 B1 | * | 8/2003 | Fossum et al. ............. | 348/246 |
| 6,819,358 B1 | * | 11/2004 | Kagle et al. ................ | 348/246 |

* cited by examiner

*Primary Examiner*—David Ometz
*Assistant Examiner*—Nhan Tran
(74) *Attorney, Agent, or Firm*—Fitzpatrick, Cella, Harper & Scinto

(57) ABSTRACT

An image processing system which processes an image signal, and determines, extracts and corrects defective pixel signals from defective pixels in a sensor array including a plurality of pixels. A given pixel signal from a pixel in the array is determined to be defective if it has a signal level below a threshold value, as determined by an extraction unit which then extracts each defective pixel signal from the defective pixels in the array. A block-forming unit forms positional information for each defective pixel having a defective pixel signal extracted by the extraction unit, with positional information for a group of such extracted defective pixel signals being formed into a block. A storage units stores, in units of blocks, positional information for the defective pixel signals. A correction unit corrects the defective pixel signals by using the positional information, in units of blocks, stored in the storage unit.

5 Claims, 11 Drawing Sheets

IMAGE PROCESSING APPARATUS

BACKGROUND OF THE INVENTION

1. Field of the Invention

The present invention relates to an image processing apparatus for determining, extracting and correcting defective pixel signals from defective pixels in an array of pixels in a sensor.

2. Description of the Related Art

Hitherto, the following method has been employed for detecting and correcting defective pixel signals from defective pixels within a sensor array. A detected defective pixel signal pattern is stored as a binary image, as shown in FIG. 1. In correcting an image taken of a subject, the stored defective pixel signal pattern is read, and the individual pixel signals are sequentially searched. If there is any defective pixel signal, it is corrected by, for example, replacing it with an average value of the surrounding pixel signals.

If a defective pixel signal pattern is not formed, coordinate values of the individual defective pixels are stored, and corrections are performed on pixel signals having the corresponding coordinates of a subject image in a manner similar to the above method.

However, the ratio of defective pixels to normal pixels within a sensor is very small, and in searching a defective pixel pattern, most of the pixels are merely skipped. Thus, searching the whole image takes time and is wasteful.

According to the technique using coordinate values of defective pixels in the sensor, a given defective pixel signal cannot be accurately corrected if there is another defective pixel near the given defective pixel in the sensor.

SUMMARY OF THE INVENTION

Accordingly, it is an object of the present invention to achieve fast and precise correction of defective pixel signals from defective pixels in a sensor array.

In order to achieve the above object, according to one aspect of the present invention, there is provided an image processing apparatus including an extraction unit for extracting a defective pixel signal from a defective pixel included in an image-pickup device having a plurality of pixels and determining a defective pixel, and a block-forming unit for forming positional information of a plurality of the defective pixels determined by the extraction unit into a block.

According to another aspect of the present invention, there is provided an image processing apparatus including a storage unit for storing, in units of blocks, positional information of a plurality of defective pixels included in an image pickup device having a plurality of pixels, and a correction unit for correcting defective pixel signals of the defective pixels in the image pickup device in units of blocks by using the positional information of the defective pixel signals stored in the storage unit.

According to still another aspect of the present invention, there is provided an image processing method including: a first step of extracting a defective pixel signal of a defective pixel included in an image pickup device having a plurality of pixels; and a second step of forming positional information of a plurality of defective pixels in the image pickup device into a block based on the extracted defective pixel signals.

According to a further aspect of the present invention, there is provided an image processing method including: a first step of reading, in units of blocks, positional information of a plurality of defective pixels included in an image pickup device having a plurality of pixels; and a second step of correcting defective pixel signals of the defective pixels in the image pickup device in units of blocks.

According to a yet further aspect of the present invention, there is provided a storage medium for storing a program which includes: a first step of extracting a defective pixel signal of a defective pixel included in an image pickup device having a plurality of pixels; and a second step of forming positional information of a plurality of defective pixels in the image pickup device into a block based on the extracted defective pixel signals.

According to a further aspect of the present invention, there is provided a storage medium for storing a program which includes: a first step of reading, in units of blocks, positional information of a plurality of defective pixels included in an image pickup device having a plurality of pixels; and a second step of correcting defective pixel signals of the defective pixels in the image pickup device in units of blocks.

According to a further aspect of the present invention, there is provided an image processing system including an image pickup device for picking up an image of a subject, an image processing apparatus performing image processing of a signal from the image pickup device, including: a storage unit for storing, in units of blocks, positional information of a plurality of defective pixels included in the image pickup device having a plurality of pixels; and a correction unit for correcting defective pixel signals of the defective pixels in the image pickup device in units of blocks by using the positional information of the defective pixel signals stored in the storage unit, a monitor for monitoring image data processed by the image processing apparatus, a network for transmitting the image data processed by the image processing apparatus, and an image database, connected to the network, storing the image data.

Further objects, features and advantages of the present invention will become apparent from the following description of the preferred embodiments with reference to the attached drawings.

DESCRIPTION OF THE PREFERRED EMBODIMENT

Figure 1:
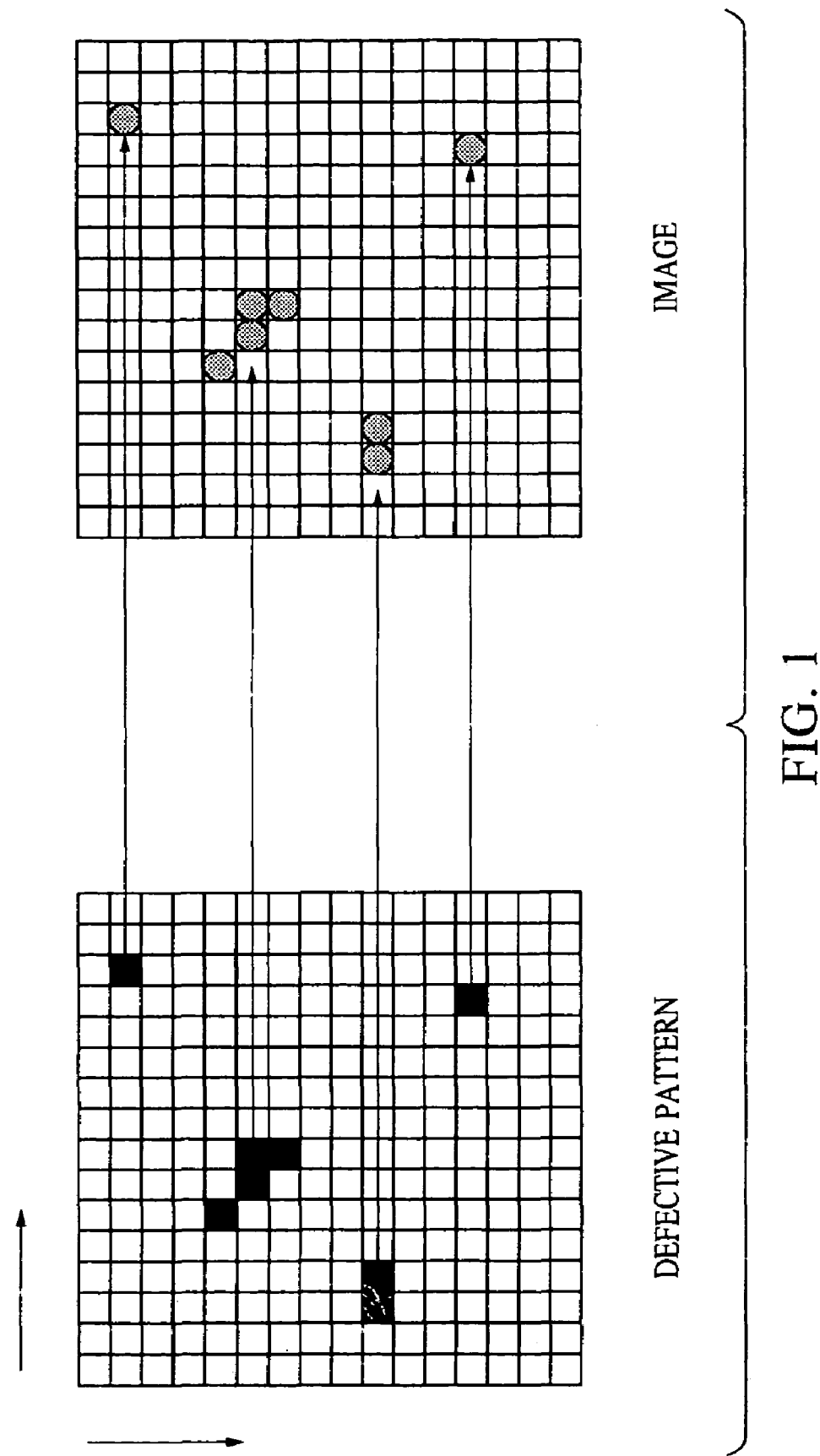
FIG. 1 schematically illustrates a conventional method of detecting and correcting defective pixel signals of defective pixels in an image pickup unit.
Figure 2:
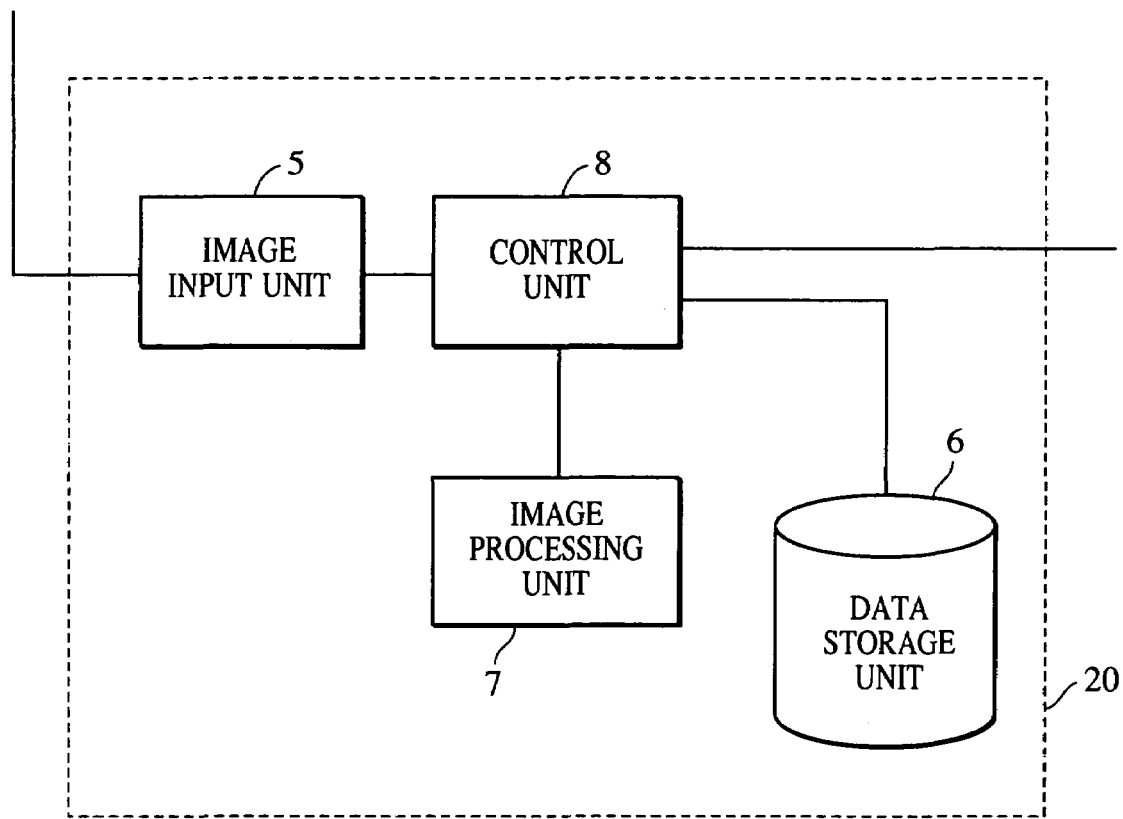
FIG. 2 is a block diagram illustrating an image processing apparatus according to an embodiment of the present invention.
Figure 3:
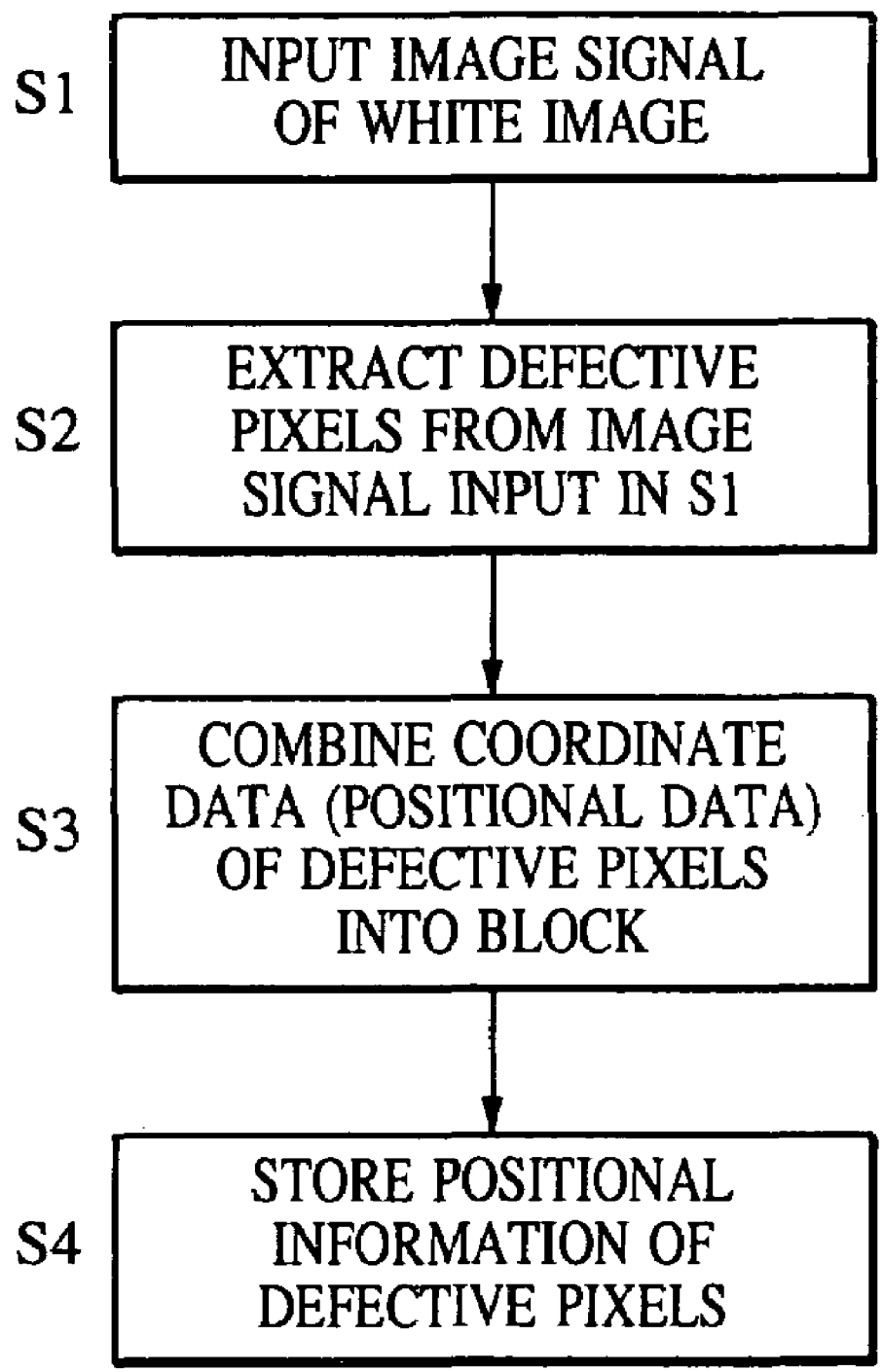
FIGS. 3 and 4 are flow charts illustrating processing executed by the image processing apparatus shown in FIG. 2.
Figure 4:
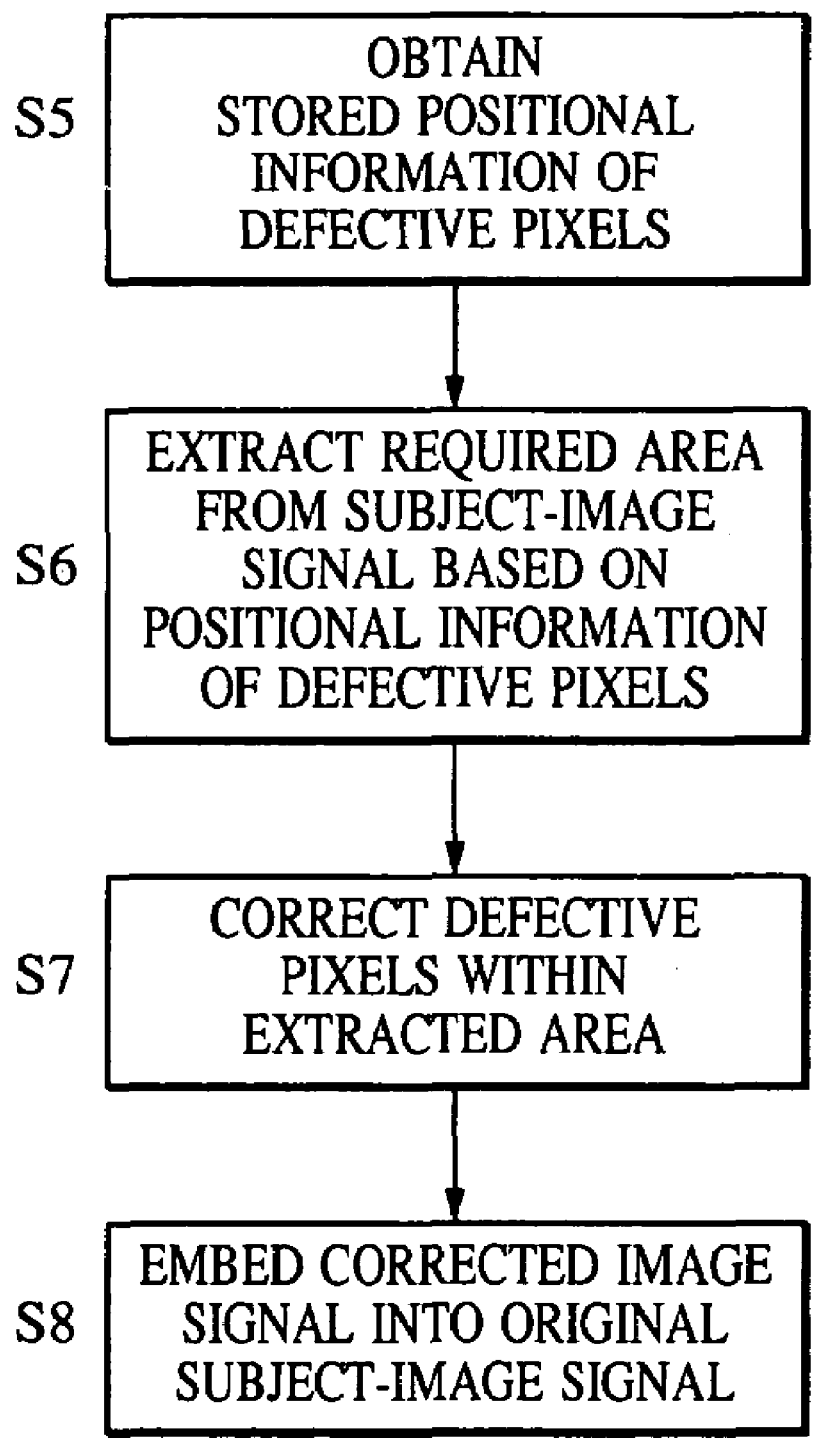

FIG. 2 illustrates the system configuration of an image processing apparatus according to an embodiment of the present invention. FIGS. 3 and 4 are flow charts illustrating processing executed by the image processing apparatus shown in FIG. 2.

The image processing apparatus shown in FIG. 2 includes the following elements. An image input unit 5, which serves as an image pickup device, receives a pixel signal from a sensor having an array of a plurality of pixels, such as from an X-ray sensor. A data storage unit 6 stores information of, for example, defective pixels. An image processing unit 7 performs image processing on the defective pixel signal input into the image input unit 5 by using the information stored in the data storage unit 6. A system control unit 8 controls the image input unit 5, the data storage unit 6, and the image processing unit 7.

Extracting defective pixel signals and storing positional information of defective pixels is discussed below with reference to FIGS. 2 and 3.

In FIG. 3, in step S1, the image input unit 5 receives a pixel signal of a white image, which has been taken without a subject, from the sensor. In step S2, the system control unit 8 causes the image input unit 5 to transmit the input pixel signal to the image processing unit 7 and instructs the image processing unit 7 to extract defective pixel signals. The image processing unit 7 then extracts all the defective pixel signals. In step S3, in response to an instruction from the system control unit 8, the image processing unit 7 combines a plurality of items of coordinate data, which indicate positional information of the defective pixels extracted by the operation in step S2, into a block. Then, in step S4, the system control unit 8 stores the blocks of coordinate data in the data storage unit 6.

The operations in steps S2 and S3 are discussed below in detail.

Concerning the extraction of defective pixel signals in step S2, a certain threshold may be set, and pixel signals having a value smaller than the threshold may be determined to be defective pixel signals from corresponding defective pixels in the sensor.

Figure 5:
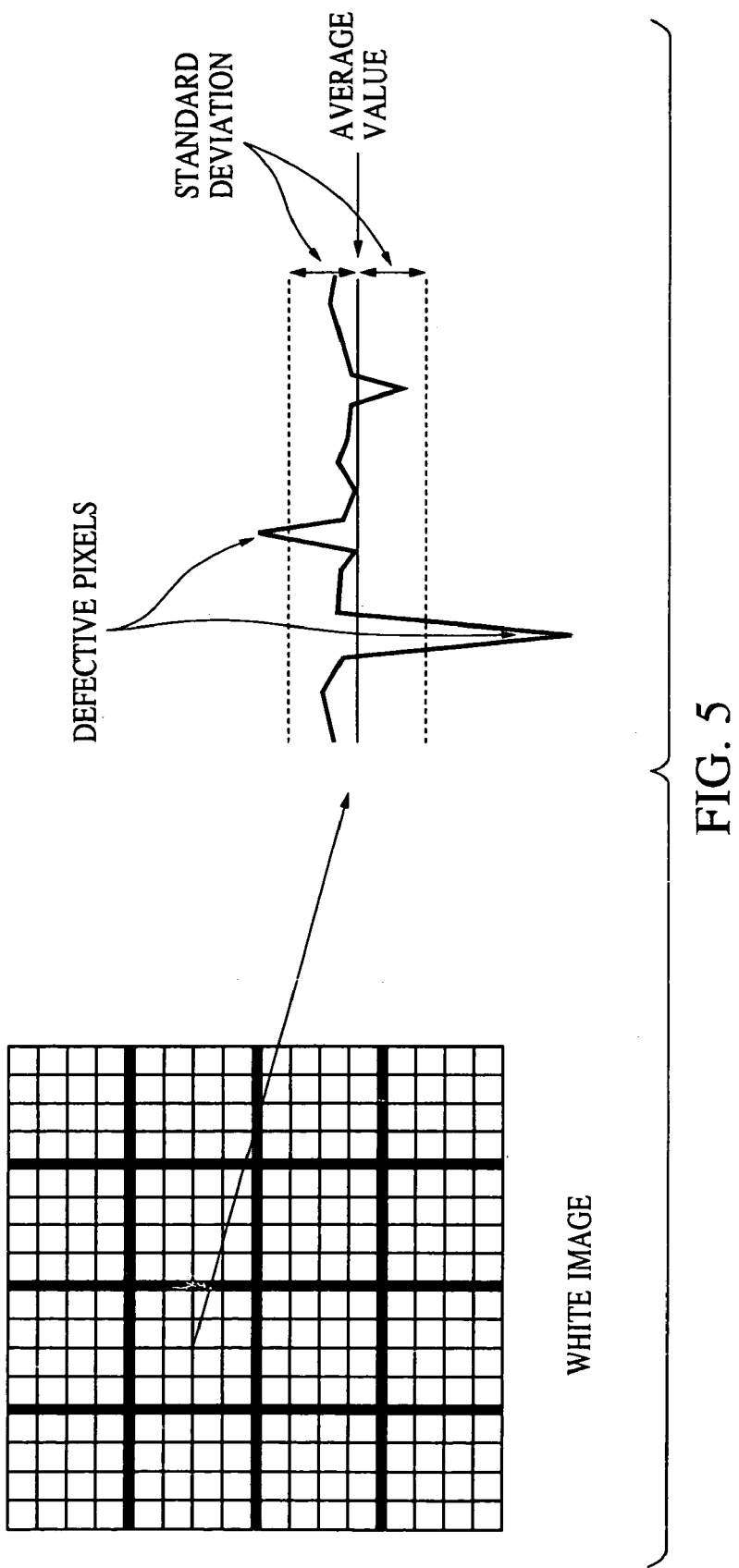
FIG. 5 illustrates a method of detecting with high precision defective pixel signals of defective pixels in an image pickup unit.

According to a technique of detecting defective pixel signals with higher precision, a white image is divided into blocks, as shown in FIG. 5, and an average signal value and a standard deviation from the average signal value within each block are determined. Then, pixel signals having a signal value which is outside a range of (the average signal value±(n×standard deviation)), where n is a specified signal value, are determined to be defective pixel signals.

Figure 6:
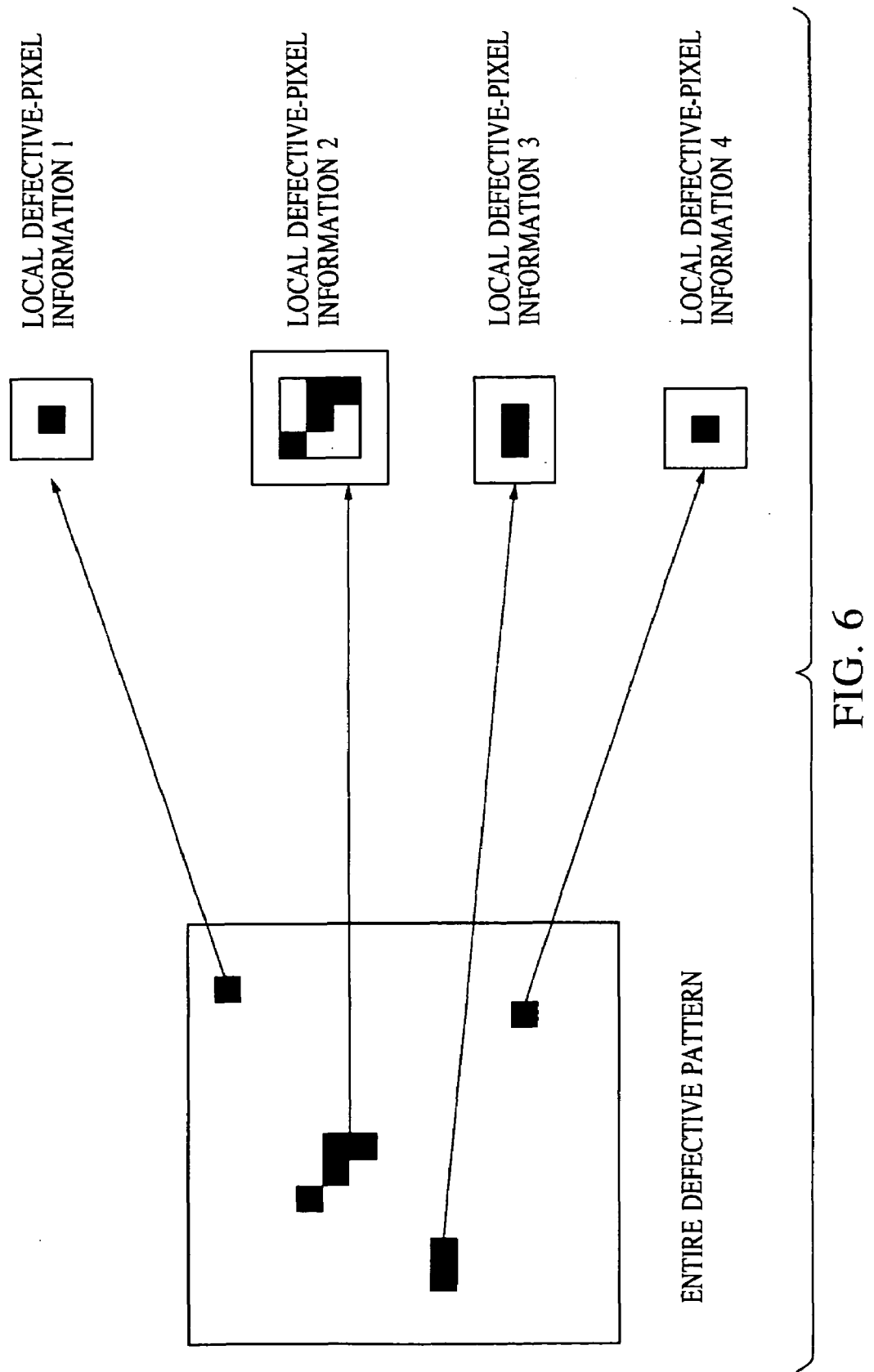
FIG. 6 illustrates extraction of defective pixel signals of defective pixels in an image pickup unit.

Correction of defective pixel signals in step S3 is as follows. The plurality of items of coordinate data of the defective pixel signals detected in step S2 are formed into one block, as shown in FIG. 6. As an example of techniques of forming the coordinate data into a block of positional information (local defective-pixel information), a run-length coding technique shown in FIG. 7 may be employed.

In run-length coding, defective pixels which are continuously located in an X direction (horizontal direction) or a Y direction (vertical direction) are integrated into a group, and the first coordinate value and the length (and the direction if necessary) of the group are coded.

A technique of forming the plurality of items of defective pixels into groups by using the above-described run-length coding is as follows. For simple representation, run-length coding is performed only in the X direction.

Figure 7:
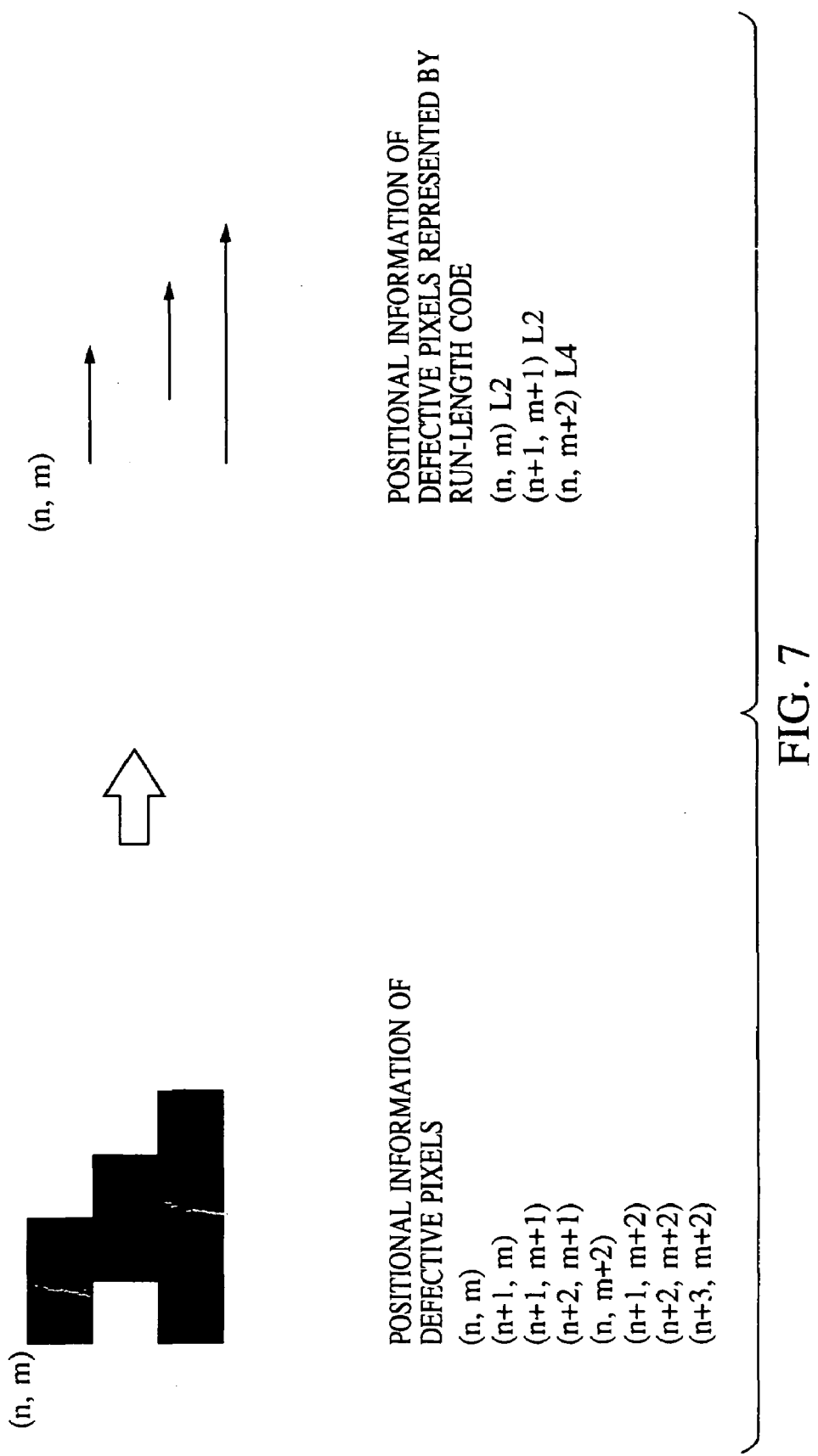
FIG. 7 illustrates run-length coding of position information.

For example, as shown in FIG. 7, since a pixel having coordinates (n,m) and a pixel having coordinates (n+1,m) are adjacent to each other with a length 2 in the X direction, they are coded into information (n,m) L2. Similarly, a pixel (n+1,m+1) and a pixel (n+2,m+1) are coded into (n+1,m+1) L2, and pixels (n,m+2), (n+1,m+2), (n+2,m+2), (n+3,m+2) are coded into (n,m+2) L4. Then, as another run-length code positioned adjacent to a given run-length code, pixels having ±1 Y coordinate are extracted. Among these pixels, pixels which are continuously placed in the X direction are grouped into a run-length code. In FIG. 7, if a given run-length code is determined to be (n,m) L2, pixels having ±1 Y coordinate and continuously located from X coordinate (n+1) are selected as a run-length code (n+1,m+1) L2 adjacent to the given run-length code (n,m) L2. The above-described operation is performed to obtain all the run-length codes, thereby integrating all the defective pixels into groups of local defective-pixel information.

The coordinate data of the defective pixels may be formed into blocks by a technique other than the above-described run-length coding. For example, by using normal x- and y-coordinate positional data, eight pixels in proximity with each other in the sensor may be checked for any adjacent defective pixels by checking the corresponding pixel signal values, and coordinate data of all the adjacent defective pixels may be determined and extracted and formed into one block based on the extracted defective pixel signals, which indicates positional information (local defective-pixel information). According to the run-length coding technique, however, the amount of positional information of defective pixels is smaller than that of the above-described technique. Thus, run-length coding is more advantageous in terms of reducing the storage area.

However, a different coding technique may be employed to reduce the storage area instead of the run-length coding technique.

Correction of defective pixel signals is discussed below with reference to FIGS. 2 and 4.

Referring to FIG. 4, in step S5, the control unit 8 obtains the local defective-pixel information stored in the data storage unit 6. Then, in step S6, the image processing unit 7 extracts an area which is required to be corrected from the subject-image signal based on the local defective-pixel information obtained in step S5. In step S7, the defective pixel signals within the extracted area are corrected. Finally, in step S8, the corrected image signal formed by the corrected defective pixel signals is embedded into the original subject-image signal by replacing the defective pixel signals. According to the above-described operation, corrections are repeatedly performed on all the items of local defective-pixel information.

The operations of steps S6 and S7 are described below in detail with reference to FIGS. 8 and 9.

Figure 8:
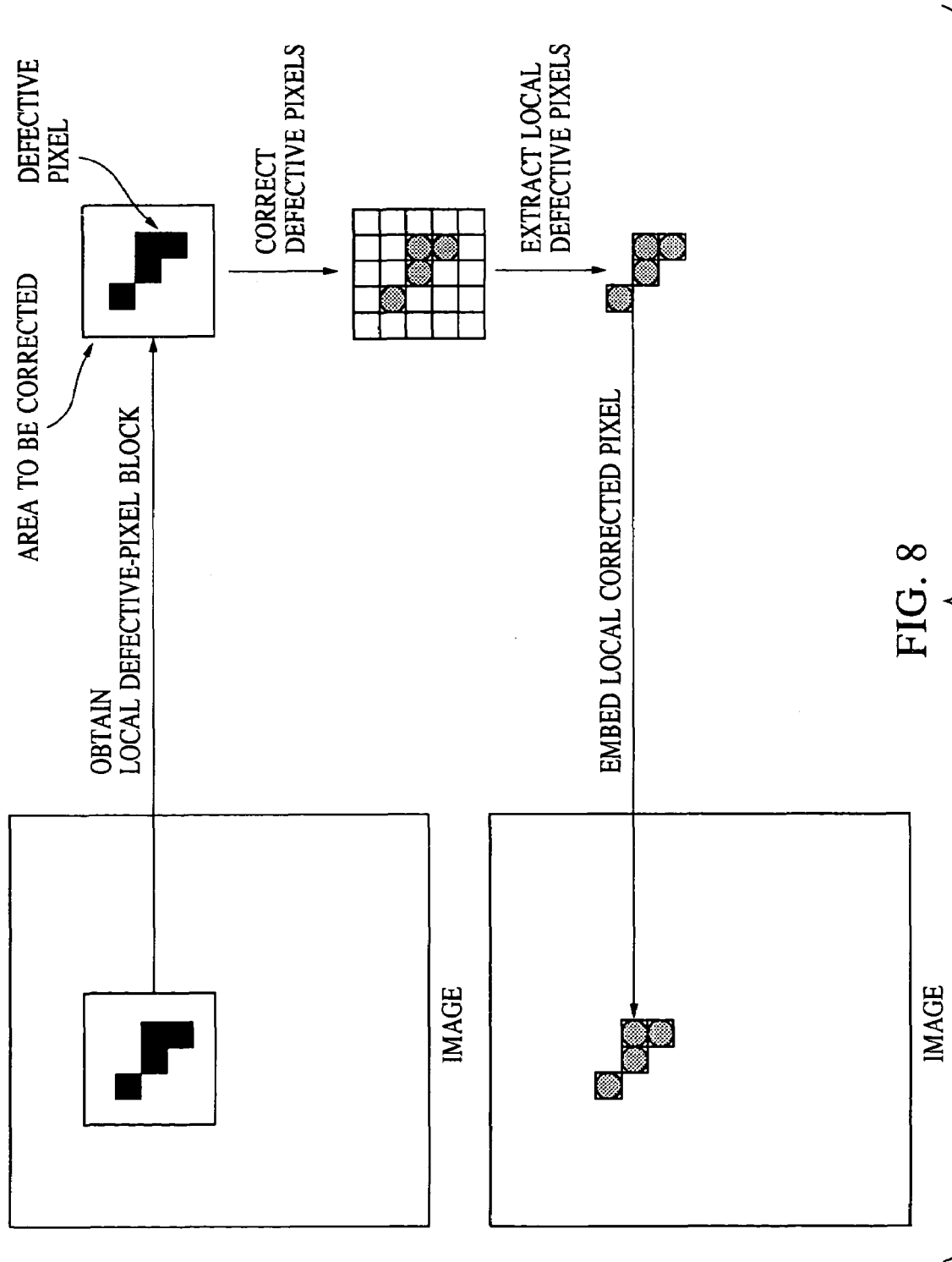
FIG. 8 illustrates extraction of defective pixel signals and embedding of corrected defective pixel signals in place of corresponding defective pixel signals in an image signal.

In step S6, a local defective-pixel block corresponding to the local defective-pixel information stored in the data storage unit 6 is extracted, as shown in FIG. 8, from an image signal obtained by taking an image of a subject. The local defective-pixel block includes defective pixels and pixels required for correcting the defective pixel signals. The local defective-pixel information may include positional information concerning only defective pixel signals or include positional information concerning both defective pixels and pixels required for correcting the defective pixel signals. If the local defective-pixel information includes only positional information of the defective pixels, an area which is required to be corrected must be calculated by the control unit 8 based on the defective-pixel positional information. If, however, the positional information of the above-described area is also included in the local defective-pixel information, the time for calculations can be reduced, thereby enabling a faster operation.

Figure 9:
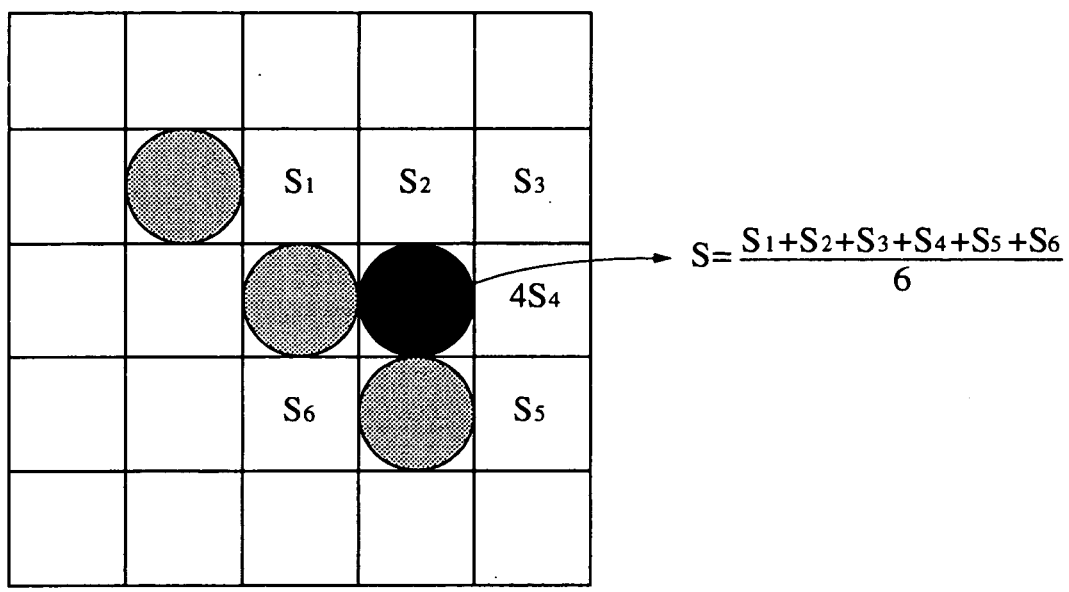
FIG. 9 illustrates correction of defective pixel signals.

In step S7, a defective pixel signal is corrected, as shown in FIG. 9, by an average of the pixel signals of the surrounding eight pixels. In this case, among the surrounding eight pixels, defective pixel signals cannot be utilized. In this embodiment, however, any defective pixel signals of defective pixels near a given defective pixel are extracted together with the defective pixel signal of the given defective pixel and are formed into a single block. It is thus possible to determine which pixel signals cannot be utilized for corrections. The corrected pixel signals (local corrected pixel signals) are then embedded into the original image in place of the defective pixel signals.

Although in the foregoing embodiment a given defective pixel signal is corrected by the average pixel signal of the surrounding eight pixels, the average pixel signal of the surrounding four pixels in the vertical and horizontal directions may be used. In this case, defective pixels obliquely adjacent to the given defective pixel in the sensor may not be necessarily formed into the same group as the given pixel, and it is essential only that defective pixels vertically or horizontally adjacent to the given defective pixel in the sensor may be formed into the same group as the given defective pixel.

The number of pixels used for corrections may be increased, in which case, the weighted mean of an increased number of pixels may be used.

Figure 10:
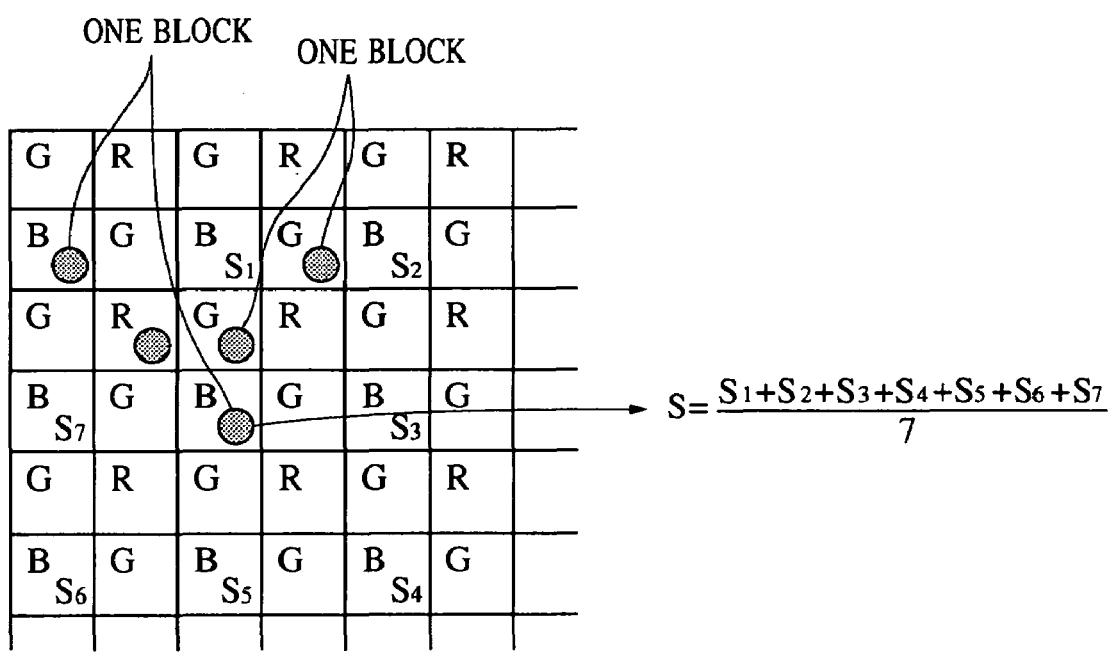
FIG. 10 illustrates correction of defective pixel signals taking the arrangement of a filter into consideration.

In using a sensor with color filters, such as the one shown in FIG. 10, a defective pixel signal of a given defective pixel of a blue (B) or red (R) color cannot be corrected by using pixel signals of adjacent pixels. Accordingly, as illustrated in FIG. 10, if a defective pixel is contained in the surrounding B-color eight pixels around a B-color pixel which is to have its defective pixel signal corrected, it is required to be formed into one group.

As discussed above, pixels can be formed into a suitable block range according to which pixel signals are to be used for correcting defective pixel signals. Positional information of the defective pixel signals by blocks is stored in the data storage unit 6, and is extracted by blocks, thereby achieving fast correction of defective pixel signals. It is also possible to determine which pixels in the sensor are defective pixels.

In the above-described embodiment, defective pixel signals are extracted and are formed into a block, and are then corrected in the image processing unit within a single image processing apparatus. However, different image processing apparatuses may be employed. That is, defective pixel signals may be extracted and formed into a block in one image processing apparatus, and may then be corrected in another image processing apparatus.

Figure 11:
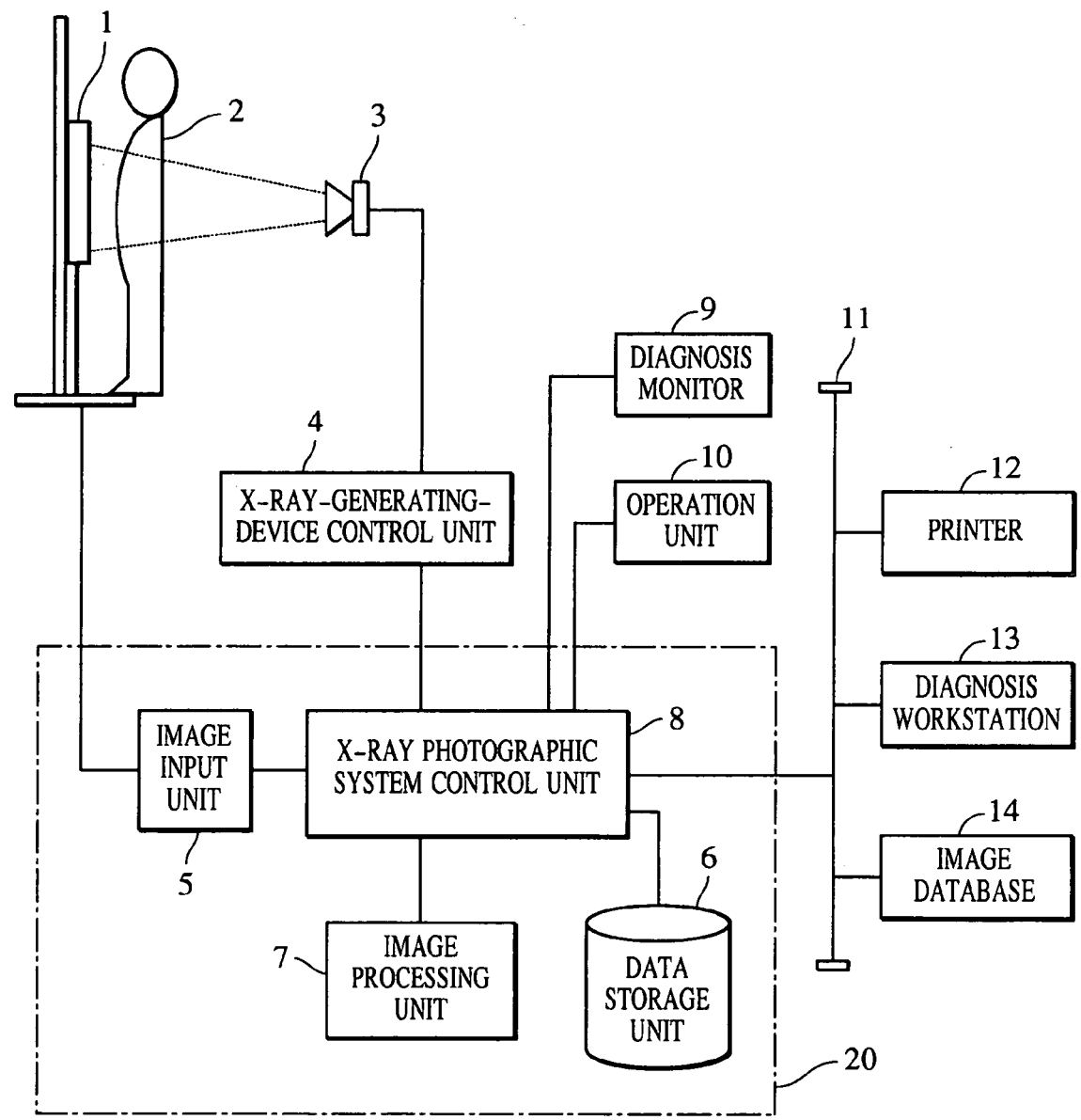
FIG. 11 illustrates the entire configuration of a digital X-ray system using an image processing apparatus according to the invention.

FIG. 11 illustrates the entire configuration of a digital X-ray system using the image processing apparatus of the foregoing embodiment.

In FIG. 11, the digital X-ray system includes an X-ray sensor 1 for receiving X rays, a subject (for example, a patient) 2, an X-ray generating device (X-ray source) 3, an X-ray-generating-device control unit 4, the image processing apparatus 20 of the above-described embodiment for performing predetermined image processing in response to a signal from the X-ray sensor 1, a diagnosis monitor 9 for monitoring an image processed in the image processing apparatus 20, an operation unit 10 for performing a predetermined operation on the image processing apparatus 20, a network 11, which is a transmission medium for transmitting the image data processed by the image processing apparatus 20, a printer 12 for outputting the image data, a diagnosis workstation 13 installed with a diagnosis monitor for monitoring image data, and an image database 14 for storing image data.

A storage medium for storing software program code which implements the functions of the above-described embodiment may be supplied to a system or a device. Then, a computer (or CPU or an MPU) of the system or the device may read the program code stored in the storage medium and execute it, so that the above-described functions can be implemented.

In this case, program code itself implements the functions of the foregoing embodiment, and a storage medium for storing the program code constitutes the present invention.

Examples of the storage medium for storing the program code include a floppy disk, a hard disk, an optical disc, a magneto-optical disk, a CD-ROM, a CD-R, a magnetic tape, a non-volatile memory card, and a ROM.

The function of the foregoing embodiment can be implemented not only by running the program code read by the computer, but also by partially or wholly executing the processing by, for example, an operating system (OS) or another application software program running in the computer according to instructions of the program code.

The present invention may also be implemented by the following modification. The program code may be read from the storage medium into a memory provided in a feature expansion board inserted into a computer or a feature expansion unit connected to the computer. Then, a CPU provided in the feature expansion board or the feature expansion unit may partially or wholly execute the processing based on the instructions of the program code, thereby implementing the above-described functions.

As is seen from the foregoing description, the present invention offers the following advantages. Fast and precise correction of defective pixel signals can be achieved. Additionally, a storage area required for defective pixel information can be reduced by utilizing, for example, run-length coding.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An image processing apparatus comprising:
   extraction means for extracting a pixel signal of an image pickup means that has a plurality of pixels, and for determining positional information of defective pixels based on the pixel signal;
   block-forming means for judging whether a plurality of the defective pixels are adjacent to each other on the basis of the positional information of the defective pixels, and encoding the adjacent defective pixels which are continuously located in one direction by using run-length codes which are information on the first coordinate values and lengths of the plurality of defective pixels, said block-forming means defining a block containing the adjacent defective pixels and peripheral, non-defective pixels for correcting the defective pixels based on said pixel signal;

storage means for storing positional information of the plurality of defective pixels and the peripheral, non-defective pixels for correcting the defective pixels within the block as regional information of the defective pixels; and correction means for correcting the defective pixels by using the peripheral, non-defective pixels of the defective pixels, wherein said correction means corrects the plurality of defective pixels within the block based on the positional information of the plurality of defective pixels and the peripheral, non-defective pixels for correcting the defective pixels within the block as region information of the defective pixels.

2. An image processing apparatus according to claim 1, wherein said extraction means judges pixels defective when the value of the pixel signal is within a predetermined range and determines the positional information of the defective pixels.

3. An image apparatus according to claim 1, wherein said block forming means selects a method for forming a block from a method used in case of correcting a defective pixel by using four non-defective pixels adjacent to the defective pixel or a method used in case of correcting a defective pixel by using eight non-defective pixels adjacent to the defective pixel.

4. An image processing method comprising:
   a first step, of extracting a pixel signal of image pickup means having a plurality of pixels and determining positional information of defective pixels based on the pixel signal;
   a second step, of judging whether a plurality of defective pixels are adjacent to each other on the basis of the positional information of defective pixels, and encoding the adjacent defective pixels which are continuously located in one direction by using run-length codes which are information on the first coordinate values and lengths of the plurality of defective pixels,
   said second step including defining a block containing the adjacent defective pixels and peripheral, non-defective pixels for correcting the defective pixels based on said pixel signal;
   a third step, of storing positional information of the plurality of defective pixels and the peripheral, non-defective pixels for correcting the defective pixels within the block as regional information of the defective pixels; and a fourth step, of correcting the defective pixels by using the peripheral, non-defective pixels of the defective pixels, wherein, in said fourth step, the plurality of defective pixels within the block are corrected based on the positional information of the plurality of defective pixels and the peripheral, non-defective pixels for correcting the defective pixels within the block as region information of the defective pixels.

5. A storage medium storing a program executed by a processor comprising:
   a first step, of extracting a pixel signal of image pickup means having a plurality of pixels and determining positional information of defective pixels based on the pixel signal;
   a second step, of judging whether a plurality of defective pixels are adjacent to each other on the basis of the positional information of defective pixels, and encoding the adjacent defective pixels which are continuously located in one direction by using run-length codes which are information on the first coordinate values and lengths of the plurality of defective pixels,
   said second step including defining a block containing the adjacent defective pixels and peripheral, non-defective pixels for correcting the defective pixels based on said pixel signal;
   a third step, of storing positional information of the plurality of defective pixels and the peripheral, non-defective pixels for correcting the defective pixels within the block as regional information of the defective pixels; and a fourth step, of correcting the defective pixels by using the peripheral, non-defective pixels of the defective pixels, wherein, in said fourth step, the plurality of defective pixels within the block are corrected based on the positional information of the plurality of defective pixels and the peripheral, non-defective pixels for correcting the defective pixels within the block as region information of the defective pixels.

* * * * *

UNITED STATES PATENT AND TRADEMARK OFFICE
CERTIFICATE OF CORRECTION

| | | |
|---|---|---|
| PATENT NO. | : 7,061,533 B1 | Page 1 of 1 |
| APPLICATION NO. | : 09/544167 | |
| DATED | : June 13, 2006 | |
| INVENTOR(S) | : Hiroyuki Urushiya | |

It is certified that error appears in the above-identified patent and that said Letters Patent is hereby corrected as shown below:

COLUMN 8

Line 5, "and" should read --and ¶--.

Signed and Sealed this

Twenty-second Day of May, 2007

JON W. DUDAS
*Director of the United States Patent and Trademark Office*